(12) United States Patent
Greetham et al.

(10) Patent No.: US 11,277,979 B2
(45) Date of Patent: Mar. 22, 2022

(54) MYCOLOGICAL BIOPOLYMERS GROWN IN VOID SPACE TOOLING

(71) Applicant: Ecovative Design LLC, Green Island, NY (US)

(72) Inventors: Lucy Greetham, Troy, NY (US); Gavin R. McIntyre, Troy, NY (US); Eben Bayer, Troy, NY (US); Jacob Winiski, Troy, NY (US); Sarah Araldi, Troy, NY (US)

(73) Assignee: Ecovative Design LLC, Green Island, NY (US)

( * ) Notice: Subject to any disclaimer, the term of this patent is extended or adjusted under 35 U.S.C. 154(b) by 695 days.

(21) Appl. No.: 14/336,455

(22) Filed: Jul. 21, 2014

(65) Prior Publication Data

US 2015/0033620 A1 Feb. 5, 2015

Related U.S. Application Data

(60) Provisional application No. 61/860,394, filed on Jul. 31, 2013.

(51) Int. Cl.
*A01G 18/00* (2018.01)
*C12P 19/26* (2006.01)
*C12N 1/14* (2006.01)

(52) U.S. Cl.
CPC ............. *A01G 18/00* (2018.02); *C12N 1/14* (2013.01); *C12P 19/26* (2013.01)

(58) Field of Classification Search
None
See application file for complete search history.

(56) References Cited

U.S. PATENT DOCUMENTS

| | | |
|---|---|---|
| 1,979,176 A | 10/1934 | Schicht |
| 2,509,984 A | 5/1950 | Morrow |
| 2,657,647 A | 11/1953 | Rapisarda |
| 2,723,493 A | 11/1955 | Stoller |
| 2,815,621 A | 12/1957 | Carter |
| 2,964,070 A | 12/1960 | Linhardt |
| 3,268,606 A | 8/1966 | Jaeger |
| 3,316,592 A | 5/1967 | Forrest |
| 3,317,375 A | 5/1967 | Molinet et al. |
| 3,421,554 A | 1/1969 | Carter |
| 3,477,558 A | 11/1969 | Fleischauer |
| 3,499,261 A | 3/1970 | Hullhorst et al. |
| 3,708,952 A | 1/1973 | Schulze et al. |
| 3,717,953 A | 2/1973 | Kuhn et al. |
| 3,782,033 A | 1/1974 | Hickerson |
| 3,810,327 A | 5/1974 | Giansante |
| 3,828,470 A | 8/1974 | Stoller |
| 3,961,938 A | 6/1976 | Iizuka et al. |
| 4,027,427 A | 6/1977 | Stoller et al. |
| 4,036,122 A | 7/1977 | Langen |
| 4,038,807 A | 8/1977 | Beardsley et al. |
| 4,063,383 A | 12/1977 | Green |
| 4,073,956 A | 2/1978 | Yates |
| 4,127,965 A | 12/1978 | Mee |
| 4,136,767 A | 1/1979 | Sarovich |
| 4,226,330 A | 10/1980 | Butler |
| 4,263,744 A | 4/1981 | Stoller |
| 4,265,915 A | 5/1981 | MacLennan et al. |
| 4,294,929 A | 10/1981 | Solomons et al. |
| 4,337,594 A | 7/1982 | Hanacek et al. |
| 4,370,159 A | 1/1983 | Holtz |
| 4,568,520 A | 2/1986 | Ackermann et al. |
| 4,620,826 A | 11/1986 | Rubio et al. |
| 4,716,712 A | 1/1988 | Gill |
| 4,722,159 A | 2/1988 | Watanabe et al. |
| 4,878,312 A | 11/1989 | Shimizu |
| 4,922,650 A | 5/1990 | Akao et al. |
| 4,960,413 A | 10/1990 | Sagar et al. |
| 5,021,350 A | 6/1991 | Jung et al. |

(Continued)

FOREIGN PATENT DOCUMENTS

| | | |
|---|---|---|
| CN | 1059662 A | 3/1992 |
| CN | 1732887 A | 2/2006 |

(Continued)

OTHER PUBLICATIONS

Zadrazil et al., Influence of CO2 Concentration on the Mycelium Growth of Three Pleurotus Species, European J. Appl. Microbiol., vol. 1, pp. 327-335 (1975).*

Heisig et al., USGS, Ground-Water Resources of the Clifton Park Area, Saratoga County, New York, 2002, retrieved from the Internet (Oct. 15, 2016): http://ny.water.usgs.gov/pubs/wri/wri014104/wrir01-4104.pdf.*

Instructables, How to Grow Oyster Mushroom Spawn (Low Tech), retrieved from the internet May 19, 2018: http://www.instructables.com/id/1-How-to-Grow-Oyster-Mushroom-Spawn-Low-Tech/.*

(Continued)

*Primary Examiner* — Scott Long
*Assistant Examiner* — Evelyn Y Pyla
(74) *Attorney, Agent, or Firm* — Knobbe, Martens, Olson & Bear, LLP

(57) ABSTRACT

A mycological biopolymer product consisting entirely of fungal mycelium is made by inoculating a nutritive substrate with a selected fungus in a sealed environment except for a void space, which space is subsequently filled with a network of undifferentiated fungal mycelium. The environmental conditions for producing the mycological biopolymer product, i.e. a high carbon dioxide ($CO_2$) content (from 5% to 7% by volume) and an elevated temperature (from 85° F. to 95° F.), prevent full differentiation of the fungus into a mushroom. There are no stipe, cap, or spores produced. The biopolymer product grows into the void space of the tool, filling the space with an undifferentiated mycelium chitin-polymer, which is subsequently extracted from the substrate and dried.

32 Claims, 5 Drawing Sheets

(56) References Cited

U.S. PATENT DOCUMENTS

| | | |
|---|---|---|
| 5,030,425 A | 7/1991 | Bowers-Irons et al. |
| 5,074,959 A | 12/1991 | Yamanaka et al. |
| 5,085,998 A | 2/1992 | Lebron et al. |
| 5,088,860 A | 2/1992 | Stockdale et al. |
| 5,123,203 A | 6/1992 | Hiromoto |
| 5,230,430 A | 7/1993 | Kidder |
| 5,306,550 A | 4/1994 | Nishiyama et al. |
| 5,335,770 A | 8/1994 | Baker et al. |
| 5,370,714 A | 12/1994 | Ogawa |
| 5,433,061 A | 7/1995 | Hutchinson et al. |
| 5,440,860 A | 8/1995 | Meli et al. |
| 5,475,479 A | 12/1995 | Hatakeyama et al. |
| 5,498,384 A | 3/1996 | Volk et al. |
| 5,503,647 A | 4/1996 | Dahlberg et al. |
| 5,511,358 A | 4/1996 | Morita et al. |
| 5,532,217 A | 7/1996 | Silver et al. |
| 5,569,426 A | 10/1996 | Le Blanc |
| 5,589,390 A | 12/1996 | Higuchi et al. |
| 5,590,489 A | 1/1997 | Hattori et al. |
| 5,598,876 A | 2/1997 | Zanini et al. |
| 5,606,836 A | 3/1997 | Insalaco et al. |
| 5,647,180 A | 7/1997 | Billings et al. |
| 5,681,738 A * | 10/1997 | Beelman ............ C05F 11/10 435/254.1 |
| 5,682,929 A | 11/1997 | Maginot et al. |
| 5,685,124 A | 11/1997 | Jandl |
| 5,711,353 A | 1/1998 | Ichikawa et al. |
| 5,802,763 A | 9/1998 | Milstein |
| 5,854,056 A * | 12/1998 | Dschida ............ C12N 1/14 435/254.1 |
| 5,888,803 A | 3/1999 | Starkey |
| 5,897,887 A | 4/1999 | Haeberli |
| 5,919,507 A | 6/1999 | Beelman et al. |
| 5,944,928 A | 8/1999 | Seidner |
| 5,948,674 A | 9/1999 | Mankiewicz |
| 5,979,109 A | 11/1999 | Sartor et al. |
| 6,041,544 A | 3/2000 | Kananen et al. |
| 6,041,835 A | 3/2000 | Price |
| 6,098,677 A | 8/2000 | Wegman et al. |
| 6,112,504 A | 9/2000 | McGregor et al. |
| 6,197,573 B1 | 3/2001 | Suryanarayan et al. |
| 6,226,962 B1 | 5/2001 | Eason et al. |
| 6,300,315 B1 | 10/2001 | Liu |
| 6,306,921 B1 | 10/2001 | Al Ghatta et al. |
| 6,329,185 B1 | 12/2001 | Kofod et al. |
| 6,349,988 B1 | 2/2002 | Foster et al. |
| 6,402,953 B1 | 6/2002 | Gorovoj et al. |
| 6,425,714 B1 | 7/2002 | Waddell |
| 6,471,993 B1 | 10/2002 | Shastri et al. |
| 6,475,811 B1 | 11/2002 | Babcock |
| 6,482,942 B1 | 11/2002 | Vittori |
| 6,491,480 B2 | 12/2002 | Waddell |
| 6,500,476 B1 | 12/2002 | Martin et al. |
| 6,523,721 B1 | 2/2003 | Nomoto et al. |
| 6,603,054 B2 | 8/2003 | Chen et al. |
| 6,620,614 B1 * | 9/2003 | Luth ............ C12M 21/16 435/291.3 |
| 6,660,164 B1 | 12/2003 | Stover |
| 6,679,301 B2 | 1/2004 | Makino et al. |
| 6,726,911 B1 | 4/2004 | Jülich et al. |
| 7,043,874 B2 | 5/2006 | Wasser et al. |
| 7,073,306 B1 | 7/2006 | Hagaman |
| 7,122,176 B2 | 10/2006 | Stamets |
| 7,179,356 B2 | 2/2007 | Aksay et al. |
| 7,395,643 B2 | 7/2008 | Franchini et al. |
| 7,514,248 B2 | 4/2009 | Gower et al. |
| 7,573,031 B2 | 8/2009 | Behar et al. |
| 7,621,300 B2 | 11/2009 | Bonney et al. |
| 7,661,248 B2 | 2/2010 | Conti et al. |
| 7,754,653 B2 | 7/2010 | Hintz |
| 7,836,921 B2 | 11/2010 | Isomura et al. |
| 8,001,719 B2 | 8/2011 | Bayer et al. |
| 8,205,646 B2 | 6/2012 | Isomura et al. |
| 8,227,224 B2 | 7/2012 | Kalisz et al. |
| 8,227,233 B2 | 7/2012 | Kalisz et al. |
| 8,241,415 B2 | 8/2012 | Wantling et al. |
| 8,298,810 B2 | 10/2012 | Rocco et al. |
| 8,313,939 B2 | 11/2012 | Kalisz et al. |
| 8,517,064 B2 | 8/2013 | Isomura et al. |
| 8,658,407 B2 | 2/2014 | Lyons et al. |
| 8,763,653 B2 | 7/2014 | Weigel et al. |
| 8,999,687 B2 | 4/2015 | Bayer et al. |
| 9,079,978 B2 | 7/2015 | Rsnen et al. |
| 9,085,763 B2 | 7/2015 | Winiski et al. |
| 9,253,889 B2 | 2/2016 | Bayer et al. |
| 9,332,779 B2 | 5/2016 | Marga |
| 9,394,512 B2 | 7/2016 | Bayer et al. |
| 9,469,838 B2 | 10/2016 | Schaak et al. |
| 9,485,917 B2 | 11/2016 | Bayer et al. |
| 9,555,395 B2 | 1/2017 | Araldi et al. |
| 9,714,180 B2 | 7/2017 | McIntyre et al. |
| 9,752,122 B2 | 9/2017 | Marga et al. |
| 9,795,088 B2 | 10/2017 | Bayer et al. |
| 9,801,345 B2 | 10/2017 | Bayer et al. |
| 9,803,171 B2 | 10/2017 | Bayer et al. |
| 9,879,219 B2 | 1/2018 | McIntyre et al. |
| 9,914,906 B2 | 3/2018 | Winiski et al. |
| 10,125,347 B2 | 11/2018 | Winiski |
| 10,144,149 B2 | 12/2018 | Araldi et al. |
| 10,154,627 B2 | 12/2018 | McIntyre et al. |
| 10,172,301 B2 | 1/2019 | McNamara et al. |
| 10,266,695 B2 | 4/2019 | Lucht et al. |
| 10,407,675 B2 | 9/2019 | Bayer et al. |
| 10,525,662 B2 | 1/2020 | Bayer et al. |
| 10,537,070 B2 | 1/2020 | Betts et al. |
| 10,583,626 B2 | 3/2020 | Bayer et al. |
| 10,589,489 B2 | 3/2020 | Bayer et al. |
| 10,687,482 B2 | 6/2020 | Ross et al. |
| 10,785,925 B2 | 9/2020 | McNamara et al. |
| 2001/0012235 A1 | 8/2001 | Schuchardt |
| 2002/0110427 A1 | 8/2002 | Waddell |
| 2002/0131828 A1 | 9/2002 | Waddell |
| 2002/0131933 A1 | 9/2002 | Delmotte |
| 2003/0017565 A1 | 1/2003 | Echigo et al. |
| 2003/0056451 A1 | 3/2003 | Pisek et al. |
| 2003/0121201 A1 | 7/2003 | Dahlberg et al. |
| 2003/0232895 A1 | 12/2003 | Omidian et al. |
| 2004/0000090 A1 | 1/2004 | Miller |
| 2004/0020553 A1 | 2/2004 | Amano |
| 2004/0166576 A1 | 8/2004 | Sadaie |
| 2004/0177585 A1 | 9/2004 | Vermette |
| 2005/0133536 A1 | 6/2005 | Kelsey et al. |
| 2005/0137272 A1 | 6/2005 | Gaserod et al. |
| 2006/0134265 A1 | 6/2006 | Beukes |
| 2006/0280753 A1 | 12/2006 | McNeary |
| 2007/0079944 A1 | 4/2007 | Amidon et al. |
| 2007/0196509 A1 | 8/2007 | Riman et al. |
| 2007/0225328 A1 | 9/2007 | Fritz et al. |
| 2007/0227063 A1 | 10/2007 | Dale et al. |
| 2007/0294939 A1 | 12/2007 | Spear et al. |
| 2008/0017272 A1 | 1/2008 | Isomura et al. |
| 2008/0046277 A1 | 2/2008 | Stamets |
| 2008/0047966 A1 | 2/2008 | Carson |
| 2008/0145577 A1 * | 6/2008 | Bayer ............ A01G 1/046 428/35.6 |
| 2008/0234210 A1 | 9/2008 | Rijn et al. |
| 2008/0295399 A1 | 12/2008 | Kawai et al. |
| 2008/0296295 A1 | 12/2008 | Kords et al. |
| 2009/0107040 A1 | 4/2009 | Vandnhove |
| 2009/0191289 A1 | 7/2009 | Lutz et al. |
| 2009/0241623 A1 | 10/2009 | Matano et al. |
| 2009/0246467 A1 | 10/2009 | Delantar |
| 2009/0272758 A1 | 11/2009 | Karwacki et al. |
| 2009/0307969 A1 | 12/2009 | Bayer et al. |
| 2009/0321975 A1 | 12/2009 | Schlummer |
| 2010/0101190 A1 | 4/2010 | Dillon |
| 2010/0158976 A1 | 6/2010 | O'Brien et al. |
| 2010/0159509 A1 | 6/2010 | Xu et al. |
| 2010/0199601 A1 | 8/2010 | Boldrini et al. |
| 2010/0227931 A1 | 9/2010 | Kuwano et al. |
| 2010/0243135 A1 | 9/2010 | Pepper et al. |
| 2010/0326564 A1 | 12/2010 | Isomura et al. |
| 2011/0094154 A1 | 4/2011 | Joaquin |
| 2011/0108158 A1 | 5/2011 | Huwiler et al. |

(56) References Cited

U.S. PATENT DOCUMENTS

| | | |
|---|---|---|
| 2011/0265688 A1 | 11/2011 | Kalisz et al. |
| 2011/0268980 A1 | 11/2011 | Kalisz et al. |
| 2011/0269209 A1 | 11/2011 | Rocco et al. |
| 2011/0269214 A1* | 11/2011 | Kalisz .................. C12N 1/14 435/246 |
| 2011/0306107 A1 | 12/2011 | Kalisz et al. |
| 2012/0000165 A1 | 1/2012 | Williams |
| 2012/0006446 A1 | 1/2012 | Isomura et al. |
| 2012/0060446 A1 | 3/2012 | Merz |
| 2012/0076895 A1 | 3/2012 | Kirejevas et al. |
| 2012/0115199 A1 | 5/2012 | Li et al. |
| 2012/0132314 A1 | 5/2012 | Weigel et al. |
| 2012/0135504 A1 | 5/2012 | Ross |
| 2012/0225471 A1 | 9/2012 | McIntyre et al. |
| 2012/0227899 A1 | 9/2012 | McIntyre et al. |
| 2012/0231140 A1 | 9/2012 | Hofmann et al. |
| 2012/0270031 A1 | 10/2012 | Guan et al. |
| 2012/0270302 A1* | 10/2012 | Bayer .................. C12N 1/14 435/254.1 |
| 2012/0315687 A1 | 12/2012 | Bayer et al. |
| 2013/0095560 A1 | 4/2013 | McIntyre et al. |
| 2013/0105036 A1 | 5/2013 | Smith et al. |
| 2013/0210327 A1 | 8/2013 | Corominas |
| 2013/0224840 A1 | 8/2013 | Bayer et al. |
| 2013/0274892 A1 | 10/2013 | Lelkes et al. |
| 2013/0309755 A1 | 11/2013 | McIntyre et al. |
| 2014/0038619 A1 | 2/2014 | Moulsley |
| 2014/0056653 A1 | 2/2014 | Scully et al. |
| 2014/0069004 A1 | 3/2014 | Bayer et al. |
| 2014/0093618 A1 | 4/2014 | Forgacs et al. |
| 2014/0173977 A1 | 6/2014 | Juscius |
| 2014/0186927 A1 | 7/2014 | Winiski et al. |
| 2014/0371352 A1 | 12/2014 | Dantin et al. |
| 2015/0038619 A1 | 2/2015 | McIntyre et al. |
| 2015/0101509 A1 | 4/2015 | McIntyre et al. |
| 2015/0197358 A1 | 7/2015 | Larsen |
| 2015/0342138 A1 | 12/2015 | Bayer et al. |
| 2015/0342224 A1 | 12/2015 | Medoff |
| 2016/0002589 A1 | 1/2016 | Winiski |
| 2016/0355779 A1 | 12/2016 | Ross |
| 2017/0000040 A1 | 1/2017 | Bayer et al. |
| 2017/0028600 A1 | 2/2017 | McIntyre et al. |
| 2017/0071214 A1 | 3/2017 | Rehage |
| 2017/0218327 A1 | 8/2017 | Amstislavski et al. |
| 2017/0253849 A1 | 9/2017 | Miller et al. |
| 2017/0253852 A1 | 9/2017 | Bayer et al. |
| 2018/0014468 A1 | 1/2018 | Ross et al. |
| 2018/0148682 A1 | 5/2018 | Ross et al. |
| 2018/0282529 A1 | 10/2018 | Kaplan-Bie |
| 2018/0368337 A1 | 12/2018 | McIntyre et al. |
| 2019/0059431 A1 | 2/2019 | Kozubal et al. |
| 2019/0090436 A1 | 3/2019 | Betts et al. |
| 2019/0284307 A1 | 9/2019 | Chase et al. |
| 2019/0322997 A1 | 10/2019 | Schaak |
| 2019/0330668 A1 | 10/2019 | Kozubal et al. |
| 2019/0338240 A1 | 11/2019 | Carlton et al. |
| 2019/0357454 A1 | 11/2019 | Mueller et al. |
| 2019/0359931 A1 | 11/2019 | Mueller et al. |
| 2019/0390156 A1 | 12/2019 | Bayer et al. |
| 2020/0024577 A1 | 1/2020 | Carlton et al. |
| 2020/0025672 A1 | 1/2020 | Scullin et al. |
| 2020/0055274 A1 | 2/2020 | Bayer et al. |
| 2020/0095535 A1 | 3/2020 | Kozubal et al. |
| 2020/0102530 A1 | 4/2020 | Winiski et al. |
| 2020/0146224 A1 | 5/2020 | Kaplan-Bie et al. |
| 2020/0157506 A1 | 5/2020 | Bayer et al. |
| 2020/0208097 A1 | 7/2020 | Winiski |
| 2020/0239830 A1 | 7/2020 | O'Brien et al. |
| 2020/0268031 A1 | 8/2020 | Macur et al. |
| 2020/0270559 A1 | 8/2020 | Macur et al. |
| 2020/0392341 A1 | 12/2020 | Smith et al. |
| 2021/0127601 A9 | 5/2021 | Kaplan-Bie et al. |

FOREIGN PATENT DOCUMENTS

| | | |
|---|---|---|
| CN | 101248869 A | 8/2008 |
| CN | 101653081 A | 2/2010 |
| CN | 106947702 A | 7/2017 |
| EP | 0226292 A1 | 6/1987 |
| EP | 1312547 A1 | 5/2003 |
| EP | 2677030 A1 | 12/2013 |
| EP | 2735318 A1 | 5/2014 |
| EP | 2875805 A1 | 5/2015 |
| EP | 2878340 A1 | 6/2015 |
| EP | 2485779 B1 | 2/2018 |
| EP | 3292769 A1 | 3/2018 |
| GB | 142800 A | 1/1921 |
| GB | 1525484 A | 9/1978 |
| GB | 2032456 A | 5/1980 |
| GB | 2165865 A | 4/1986 |
| IN | 358266 B | 7/2020 |
| JP | H03234889 A | 10/1991 |
| JP | H049316 A | 1/1992 |
| JP | 6111510 B1 | 4/2017 |
| KR | 20050001175 A | 1/2005 |
| KR | 101851655 B1 | 4/2018 |
| WO | WO 1999/024555 | 5/1999 |
| WO | WO 2001/087045 | 11/2001 |
| WO | WO 2005/067977 | 7/2005 |
| WO | WO 2008/025122 | 3/2008 |
| WO | WO 2008/073489 | 6/2008 |
| WO | WO 2010/005476 | 1/2010 |
| WO | WO 2012/122092 | 9/2012 |
| WO | WO 2014/039938 | 3/2014 |
| WO | WO 2014/195641 | 12/2014 |
| WO | WO 2016/149002 | 9/2016 |
| WO | WO 2017/056059 | 4/2017 |
| WO | WO 2017/120342 | 7/2017 |
| WO | WO 2017/136950 | 8/2017 |
| WO | WO 2017/151684 | 9/2017 |
| WO | WO 2017/205750 | 11/2017 |
| WO | WO 2018/011805 | 1/2018 |
| WO | WO 2018/014004 | 1/2018 |
| WO | WO 2018/064968 | 4/2018 |
| WO | WO 2018/183735 | 10/2018 |
| WO | WO 2018/189738 | 10/2018 |
| WO | WO 2019/046480 | 3/2019 |
| WO | WO 2019/099474 | 5/2019 |
| WO | WO 2019/178406 | 9/2019 |
| WO | WO 2019/217175 | 11/2019 |
| WO | WO 2019/226823 | 11/2019 |
| WO | WO 2019/246636 | 12/2019 |
| WO | WO 2020/023450 | 1/2020 |
| WO | WO 2020/072140 | 4/2020 |
| WO | WO 2020/082043 | 4/2020 |
| WO | WO 2020/082044 | 4/2020 |
| WO | WO 2020/102552 | 5/2020 |
| WO | WO 2020/106743 | 5/2020 |
| WO | WO 2020/176758 | 9/2020 |
| WO | WO 2020/186068 | 9/2020 |
| WO | WO 2020/186169 | 9/2020 |
| WO | WO 2020/237201 | 11/2020 |

OTHER PUBLICATIONS

Agnese et al., "Investigating the Influence of Various Plasticizers on the Properties of Isolated Films of Polyvinyl Acetat". The 37th Annual meeting and Exposition of the Controlled Release Society, Jul. 2010, Portland, Or U.S.A.

Amsellem et al., "Long-term preservation of viable mycelia of two mycoherbicidal organisms". Crop Protection (1999) 18: 643-649.

Angelini et al., "Effect of antimicrobial activity of Melaleuca alternifolia essential oil on antagonistic potential of Pleurotus species against Trichoderma harzianum in dual culture." World J Microbiol Biotech. (2008) 24(2): 197-202.

Antón et al., "PimM, a PAS Domain Positive Regulator of Pimaricin Biosynthesis in Streptomyces natalensis." Microbiol. (2007) 153: 3174-3183.

Appels et al., "Hydrophobin gene deletion and environmental growth conditions impact mechanical properties of mycelium by

(56) References Cited

OTHER PUBLICATIONS affecting the density of the material." Scientific Reports (2018) 8(1): 1-7.

Arshad et al., "Tissue engineering approaches to develop cultured meat from cells: a mini review." Cogent Food & Agriculture (2017) 3(1): 1320814 in 11 pages.

Ashiuchi et al., "Isolation of Bacillus subtilis (chungkookjang), a poly-gamma-glutamate producer with high genetic competence". Appl Microbiol Biotechnol. (2011) 57: 764-769.

Bajaj et al., "Poly (glutamic acid)—An emerging biopolymer of commercial interest". Bioresource Tech. (2011) 102(10): 5551-5561.

Baysal et al., "Cultivation of oyster mushroom on waste paper with some added supplementary materials". Biosource Technology (2003) 89: 95-97.

Begum et al., "Bioconversion and saccharification of some lignocellulosic wastes by Aspergillus oryzae ITCC-4857.01 for fermentable sugar production". Elect J Biotech. (2011) (14)5: 3 in 8 pages.

Belardinelli et al., "Actions of Adenosine and Isoproterenol on Isolated Mammalian Ventricular Myocytes." Circulation Res. (1983) 53(3): 287-297.

Belay et al., "Preparation and Characterization of Graphene-agar and Graphene Oxide-agar Composites." JOAPS (2017) 134(33): 45085.

Binder et al., "Phylogenetic and phylogenomic overview of the Polyporales". Mycologia (Nov. 12, 2013) 105(6): 1350-1373.

Blanchette et al., "Fungal mycelial mats used as textile by indigenous people of North America", Mycologia (Feb. 20, 2021) pp. 1-7.

Booth et al., "Potential of a dried mycelium formulation of an indigenous strain of Metarhizium anisopliae against subterranean pests of cranberry." Biocontrol Science and Technology (2000) 10: 659-668.

Bormann et al., "Characterization of a Novel, Antifungal, Chitin-binding Protein from Streptomyces Tendae Tu901 that Interferes with Growth Polarity." J Bacter. (1999) 181(24): 7421-7429.

Bowman et al., "The structure and synthesis of the fungal cell wall". Bioassays (2006) 28(8): 799-808.

Bružauskaite et al., "Scaffolds and Cells for Tissue Regernation: Different Scaffold Pore Sizes—Different Cell Effects." Cytotechnology (2016) 68(3): 355-369.

Byrd, "Clean meat's path to your dinner plate", The Good Food Institute, website accessed Nov. 14, 2018, https://www.gfi.org/clean-meats-path-to-commercialization; 11 pages.

Cerimi et al., "Fungi as source for new bio-based materials: a patent review", Fungal Biol Biotechnol. (2019) 6: 17; 10 pgs.

Chai et al., "β-Glucan Synthase Gene Overexpression and β-Glucans Overproduction in Pleurotus ostreatus Using Promoter Swapping". PLoS ONE (2013) 8(4): e61693 in 7 pages.

Chaudhary et al., "Understanding rice hull ash as fillers in polymers: a review". Silicon Chemistry (2002) 1:281-289.

Chi et al., "Can Co-culturing of Two White-rot Fungi Increase Lignin Degradation and the Production of Lignin-degrading Enzymes?" Inter'l Biodeter Biodegrad. (2007) 59(1): 32-39.

Collins English Dictionary, "Mould", retrieved from http://collinsdictionary.com/dictionary/english/mould, archived on Apr. 8, 2015, 3 pages.

Dias et al., "Synthesis and characterization of chitosan-polyvinyl alcohol-bioactive glass hybrid membranes". Biomatter (2011) 1(1): 114-119.

Elleuche et al., "Carbonic anhydrases in fungi". Microbiology (2010) 156: 23-29.

Elsacker et al., "Growing living and multifunctional mycelium composites for large-scale formwork applications using robotic abrasive wire-cutting", Construction Bldg Mater. (2021) 283: 122732 in 16 pages.

Fleet G.H., "Cell walls", in The Yeasts, by Rose et al. [Eds.] 2nd Edition. vol. 4. London: Academic Press. (1991) pp. 199-277.

Frandsen R.J.N., "A guide to binary vectors and strategies for targeted genome modification in fungi using Agrobacterium tumefaciens-mediated transformation". J Microbiol Methods (2011) 87: 247-262.

Gardening KnowHow, Perlite Soil Info: Learn About Perlite Potting Soil, online at www.gardeningknowhow.com/garden-how-to/soil-fertilizers/perlite-potting-soil.htm downloaded on Dec. 16, 2015., 3 pages.

Glowacki et al., "Bioconjugation of Hydrogen-bonded Organic Semiconductors with Functional Proteins." J Mate Chem. C (2015) 3(25): 6554-6564.

Goodell et al., "Fungal Decay of Wood: Soft Rot-Brown Rot-white Rot". In Development of Commercial Wood Preservatives; Schultz et al. [Ed.] ACS Symposium Series; American Chemical Society, Washington, D.C. (2008), Chapter 2, pp. 9-31.

Google Report, Complete colonization substrate mushroom (2 pages) Jan. 30, 2018., 2 pages.

Google Dictionary Definition "Composite", downloaded on Nov. 21, 2018; 1 page.

Gourmet Mushroom, Inc., "What is Mushroom?" —Mushroom Facts Mushroom Information—Educational & Science Projects (2004). Downloaded from www.gmushrooms.com, on Nov. 27, 2017; 5 pages.

Greetham et al., "Pheotypic characterisation of Saccharomyces sensu stricto to Inhibitory Compounds Released During the Deconstruction of Lignocellulosic Material." 3th International Congress on Yeasts, ICY, Aug. 26-30, 2012, Madison, USA; 1 page.

Griffin et al., "Regulation of macromolecular synthesis, colony development and specific growth rate of Achlya bisexualis during balanced growth". J General Microbiol. (1974) 80(2): 381-388.

Growers Supply. "Horticultural Coarse Perlite—4 Cubic Fee—Growers Supply". URL: https://growerssupply.com; Growers Supply 2012; www.growerssupply.com/farm/supplies/prod1:gs_growing_mediums:pg111049.html; downloaded Dec. 14, 2020 in 3 pages.

Haneef et al., "Advanced Materials from Fungal Mycelium: Fabrication and Tuning of Physical Properties", Scientific Reports 7(1): 1-11; DOI: 10.1038/srep41292, Jan. 24, 2017.

Heinzkill et al., "Characterization of laccases and peroxidases from wood-rotting fungi (family Coprinaceae)." Appl Environ Microbiol. (1998) 64: 1601-1606.

Home Depot "Miracle Gro® Perlite Mix", retrieved from the internet: http://homedepot.eom/p/Miracle-Gro-8-pt-Perlite-Mix-74278430/204502291; 2 pages.

Home Depot "Pennington—Fast Acting Gypsum", retrieved from the internet: http://homedepot.eom/p/Miracle-Gro-8-pt-Perlite-Mix-74278430/204502291; 2 pages.

Horton et al., "Regulation of Dikaryon-Expressed Genes by FRT1 in the Basidiomycete Schizophyllum commune". Fungal Genet Biol. (1999) 26(1): 33-47.

Howden et al., "The effects of breathing 5% CO2 on human cardiovascular responses and tolerance to orthostatic stress". Exper. Physiol. (2004) 89(4): 465-471.

Hüttner et al., "Recent advances in the intellectual property landscape of filamentous fungi", Fungal Biol Biotechnol. (2020) 7:16; 17 pgs.

Hyde et al., "The amazing potential of fungi: 50 ways we can exploit fungi industrially". Fungal Diversity (2019) 97(1): 1-136.

Jones et al., "Leather-like material biofabrication using fungi", Nature Sustainability (2020) https://doi.org/10.1038/s41893-020-00606-1, Sep. 7, 2020.

Kamzolkina et al., "Micromorphological features of Pleurotus pulmonarius (Fr.) Quel, and P. ostreaturs (Jacq.) P. Kumm. Strains in pure and binary culture with yeasts". Tsitologiia (2006) 48(2): 153-160.

Kemppainen et al., "Transformation of the Mycorrhizal Fungus Laccaria Bicolor using Agrobacterium tumefaciens." Bioengin Bugs (2011) 2(1): 38-44.

Kerem et al., "Effect of Mananese on Lignin Degradation by Pleurotus ostreatus during Solid-State Fermentation". Applied and Environmental Microbiology (1993) 59(12): 4115-4120.

(56) References Cited

OTHER PUBLICATIONS

Kilaru et al., "Investigating dominant selection markers for Coprinopsis cinerea: a carboxin resistance system and re-evaluation of hygromycin and phleomycin resistance vectors". Curr Genet. (2009) 55: 543-550.

Kim et al., "Current Technologies and Related Issues for Mushroom Transformation." Mycobiology (2015) 43(1): 1-8.

Kotlarewski et al., "Mechanical Properties of Papua New Guinea Balsa Wood." European J Wood Wood Products (2016) 74(1): 83-89.

Kück et al., "New tools for the genetic manipulation of filamentous fungi". Appl Microbiol Biotechnol. (2010) 86: 51-62.

Kües, U., "Life History and Development Processes in the Basidiomycete Coprinus Cinereus." Micro Molecular Biol Rev. (2000) 64(2): 316-353.

Kuhar et al., by Ingredi Potassium Sorbate vs Campden Tablets in Wine Making; Jun. 4, 2018. [online]; Retrieved from the Internet <URL: https://ingredi.com/blog/potassium-sorbate-vs-campden-tables-in-wine-making/>; 2 pages.

Kuo, 2005-2006. Glossary of Mycological Terms. Mushroom Expert. Com., pp. 1-13; downloaded from http://www.mushroomexpert.com/glossary.html (May 8, 2015).

Li et al., "Preparation and Characterization of Homogeneous Hydroxyapatite/Chitosan Composite Scaffolds via In-Situ Hydration". J Biomaterials Nanobiotech. (2010) 1: 42-49.

Luo et al., "Coprinus comatus: a basidiomycete fungus forms novel spiny structures and infects nematode." Mycologia (2004) 96(6): 1218-1225.

McPherson et al., "Dissolvable Antibiotic Beads in Treatment of Periprosthetic Joint Infection and Revision Arthroplasty: The Use of Synthetic Pure Calcium Sulfate (Stimulan®) Impregnated with Vancomycin & Tobramycin." Reconstructive Review (2013) 3(1) 12 pages.

Merriam-Webster, "Chamber" dictionary definition; https://www.merriam-webster.com/dictionary accessed 2017-07-10; in 4 Pages.

Merriam-Webster, "pack" Thesaurus definition; https://www.merriam-webster.com/thesaurus; synonyms accessed 2019-08-19; in 10 Pages.

Michielse et al., "Agrobacterium-mediated Transformation of the Filamentous Fungus Aspergillus Awamori." Nature Protocols (2008) 3(10): 1671-1678.

Mitchell et al., [Eds.] "Solid-State Fermentation Bioreactors." Springer Verlag, Berlin/Heidelberg (2006); TOC in 12 Pages.

Moore D., "Fungal Morphogenesis." Cambridge University Press, Cambridge, UK; (1998) TOC in 8 Pages.

Moore D., "Tolerance of Imprecision in Fungal Morphogenesis." In Proceedings of the 4th Meeting on the Genetics and Cellular Biology of Basidiomycetes (1998, March) pp. 13-19.

Mushroom Growers' Handbook 1, "Oyster Mushroom Cultivation". Part II, Chapter 5, (2005) pp. 75-85.

Mushroom Growers' Handbook 2, "Shiitake Bag Cultivation", Part I Shiitake. Published by Mush World (2005) Chapter 4, pp. 73-90 and pp. 105-109.

Naknean et al., "Factors Affecting Retention and Release of Flavor Compounds in Food Carbohydrates." Inter'l Food Res J. (2010) 17(1): 23-34.

Newaz et al., "Characterization of Balsa Wood Mechanical Properties Required for Continuum Damage Mechanics Analysis." Proceedings of the Institution of Mechanical Engineers, Part L: Journal of Materials: Design and Applications (2016) 230(1): 206-218.

Norvell L., Fungi Biology. Encyclopedia.(2002); 2 pages.

Novoselova et al., "Cocultivation of Pleurotus ostreatus (Jacq.) P. Kumm. with yeasts". Moscow University Biol Sciences Bulletin (2011) 66(3): 102-105.

Nussinovitch "Polymer Macro-and Micro-Gel Beads: Fundamentals and Applications", DOI 10.1007/978-1-4419-6618_2, Springer Science & Business Media LLC (2010) TOC in 8 Pages.

Paz et al., "One Step Contruction of Agrobacterium-Recombination-ready-plasmids (OSCAR): An Efficient and Robust Tool for ATMT Based Gene Deletion Construction in Fungi." Fungal Gen Biol. (2011) 48(7): 677-684.

Peksen et al., "Favourable Culture Conditions for mycelial growth of Hydnum repandum, a medicinal mushroom." African Journal of Traditional, Complementary and Alternative Medicines (2013) 10(6): 431-434.

Peng et al., "Microbial biodegradation of polyaromatic hydrocarbons". FEMS Microbiol Rev. (2008) 32:927-955.

Perez et al., "Myxococcus xanthus induces actinorhodin overproduction and aerial mycelium formation by Streptomyces coelicolor." Microbial Biotech. (2011) 4(2): 175-183.

Philippoussis et al., "Production of Mushrooms Using Agro-Industrial Residues as Substrates", in Biotechnology for Agro-Industrial Residues, Chapter 9, (2009) pp. 163-187.

Poppe J., Mushroom Growers' Handbook 1,2004, Part II. Chapter 5, "Substrate", pp. 80-81.

Pompei et al., "The Use of Olive Milling Waste-Water for the Culture of Mushrooms on Perlite". Acta Horticulturae (1994) 361:179-185.

Rai et al., "Production of Edible Fungi", in Fungal Biotechnology in Agricultural, Food, and Environmental Applications, D.K. Arora [Ed.], Marcel Dekker, Inc., (2003), Chapter 21, pp. 383-404.

Ross, P "Pure Culture" 1997-Present; URL: <http://billhoss.phpwebhosting.com/ross/index.php7kind>; downloaded Dec. 14, 2016 in 11 pages.

Royse et al., "Influence of substrate wood-chip particle size on shiitake (Lentinula edodes) yield". Bioresource Tehnology (2001) 76(3): 229-233.

Sapak et al., "Effect of endophytic bacteria on growth and suppression of Tganoderma infection in oil palm". Int J Agric Biol. (2008) 10(2): 127-132.

Schaner et al., "Decellularized Vein as a Potential Scaffold for Vascular Tissue Engineering." J Vascular Surg. (2004) 40(1): 146-153.

Schirp et al., "Production and characterization of natural fiber-reinforced thermoplastic composites using wheat straw modified with the fungus Pleurotus ostreatus". J Appl. Polym. Sci. (2006) 102:5191-5201.

Scholtmeijer et al., "Effect of introns and AT-rich sequences on expression of the bacterial hygromycin B resistance gene in the basidiomycete Schizophyllum commune". Appl Environ Microbiol. (2001) 67(1): 481-483.

Schuurman J., "Unique agar Pearls." YouTube video; Feb. 16, 2012, <https://www.youtube.com/watch?v=8Gq I Iohetpq>; 1 page.

Science Daily, May 7, 2007, retrieved from the Internet; http://www.sciencedaily.com/releases/2007/U.S. Appl. No. 05/070,506Q85628.htm., 3 pages.

Seamon K.B., "Forskolin: Unique Diterpene Activator of Adenylate Cyclase in Membranes and in Intact Cells." PNAS (1981) 78(6): 3363-3367.

Sinotech et al., (2015): retrieved from the Internet http://www.sinotech.com/compressionAndTransferMolding.html., 4 pages.

Slater, M. "Young SoRo Entrepreneur Develops Environmentally Friendly Insulation." The Herald of Randolph. Jun. 21, 2007, pp. 1-2.

Staib et al., "Differential expression of the NRG1 repressor controls species-specific regulation of chlamydospore development in Candida albicans and Candida dubliniensis." Molecular Microbiol. (2005) 55(2): 637-652.

Stamets P., "Mycelium Running". Ten Speed Press (2005); pp. 18, 56, 58, 59, 85, 149, 157, 160 and 291 only.

Stamets P., "Growing Gourmet and Medicinal Mushrooms", (Undated) Chapter 21; p. 363.

Stanev et al., "Open Cell Metallic Porous Materials Obtained Through Space Holders. Part I: Production Methods, A Review". JMSE (2016) 139(5): 21 pages.

Stephens et al., "Bringing Cultured Meat to Market: Technical, Socio-political, and Regulatory Challenges in Cellular Agriculture." Trends in Food Science & Technology (2018) 78:155-166.

Sundari et al., "Freeze-drying vegetative mycelium of Laccaria fraterna and its subsequent regeneration". Biotechnology Techniques (1999) 13:491-495.

Tartar et al., "Differential expression of chitin synthase (CHS) and glucan synthase (FKS) genes correlates with the formation of a

(56) References Cited

OTHER PUBLICATIONS modified, thinner cell wall in in vivo-produced Beauveria bassiana cells." Mycopathologia (2005) 160(4): 303-314.

Téllez-Jurado et al., "Expression of a heterologous laccase by Aspergillus niger cultured by solid-state and submerged fermentations." Enzyme Microbial Tech. (2006) 38(5): 665-669.

Téllez-Téllez et al., "Growth and laccase production by Pleurotus ostreatus in submerged and solid-state fermentation." Appl Microbiol Biotechnol. (2008) 81(4): 675-679.

Thomas et al., "Growing Orchids in Perlite". In Perlite Plant Guide, The Schundler Company 1951, pp. 1-6, downloaded from http://www.schundler.com/index.html, archived on May 11, 2015.

Timberpress—"How Do Mushrooms Grow So Quickly.", downloaded from the internet: www.timberpress.com/blog/2017/01/how-do-mushrooms-grow-so-quickly, download Feb. 27, 2018 in 7 Pages.

Ugalde U., "Autoregulatory Signals in Mycelial Fungi" in The Mycota: A Comprehensive Treatise on Fungi as Experimental Systems for Basic and Applied Research. K. Esser [Ed.] Springer Publisher, 2nd Edition (2006) Chapter 11; pp. 203-213.

Universal Oil Field, "Sawdust", downloaded from universaloilfield.org on Aug. 23, 2018, 4 pages.

Vara et al., "Cloning and expression of a puromycin N-acetyl transferase gene from Streptomyces alboniger in Streptomyces lividans and *Escherichia coli*". Gene (1985) 33(22): 197-206.

Visser et al., "Pseudoxylaria as stowaway of the fungus-growing termite nest: Interaction asymmetry between Pseudoxylaria, Termitomyces and free-living relatives". Fungal Ecology (2011)4(5): 322-332.

Volk (2003) "Tom Volk's Fungus of the Month for Oct. 1998". This month's fungus is Pleurotus ostreatus; the Oyster mushroom, pp. 1-4, downloaded from http://botit.botany.wisc.edu/toms_fungi/oct98.html on May 8, 2015.

Wang et al., "Influence of fungal elicitors on biosynthesis of natamycin by Streptomyces natalensis HW-2". Appl Microbiol Biothechnol. (2003) 97: 5527-5534.

Wikipedia, "Water gel (plain)", Wikipedia Contributors downloaded Aug. 21, 2017 in 1 Page.

Wikipedia, "Wood", downloaded on Nov. 26, 2018, 1 page.

Xiao et al., "A Water-soluble Core Material for Manufacturing Hollow Composite Sections." Comp. Structures (2017) 182: 380-390.

Yang et al., "Medicinal Mushroom Ganoderma lucidum as a Potent Elicitor in Production of t-Resveratrol and t-Peceatannol in Peanut Calluses". J Agric Food Chem. (2010) 58(17): 9518-9522.

Zimin et al., "The MaSuRCA genome assembler". Bioinformatics (2013) 29(21): 2669-2677.

Grant, James. J.—"An investigation of the airflow in mushroom growing structures, the development of an improved, three-dimensional solution technique for fluid flow and its evaluation for the modelling of mushroom growing structures", Doctoral Thesis Sep. 2002; 326 pages.

Aninori et al., "Advanced mycelium materials as potential self-growing biomedical scaffolds." Scientific reports (2021) 11(1): 1-14.

Bartnicki-Garcia, "Cell wall chemistry, morphogenesis, and taxonomy of fungi", Annual Review Microbiol. (1968) 22(1): 87-108.

Cha et al., "Biomimetic synthesis of ordered silica structures mediated by block copolypeptides". Nature (2000) 403(6767): 289-292.

Dugdale J. "This new surf company is making boards of mushrooms". Blog post—Jun. 25, 2015.

Halseide P., "Cutting brick the safe way". The Aberdeen Group (1988) Publication #M880354 in 2 pages.

Hidayat et al., "Characterization of polylactic acid (PLA)/kenaf composite degradation by immobilized mycelia of Pleurotus ostreatus". Inter Biodeter Biodegrad. (2012) 71: 50-54.

Highland Woodworking, "Making Thin Lumber and Veneer Out of Ordinary Boards", Sales Website (2017) in 3 pages.

Holt et al., "Biobased Composition Boards Made from Cotton Gin and Guayule Wastes: Select Physical and Mechanical Properties", Int J Mater Prod Tech. (2009) 36: 104-114.

Islam et al., "Morphology and mechanics of fungal mycelium", Scientific Reports, (2017) 7(1): 1-12.

Jiang et al., "Bioresin Infused then Cured Mycelium-based Sandwich-structure Biocomposites: Resin Transfer Molding (RTM) Process, Flexural Properties, and Simulation." J Cleaner Production (2019) 207: 123-135.

Jones et al., Chitin-chitosan Thin Films from Microbiologically Upcycled Agricultural Byproducts. In 13th International Conference on the Mechanical Behavious of Materials, Melbourne, Australia (Jun. 2019) p. 66; in 7 pages.

Kerem et al., "Chemically defined solid-state fermentation of Pleurotus Ostreatus". Enzyme Microbiol Tech. (1993) 15(9): 785-790.

Kokubo et al., "Ca,P-rich layer formed on high-strength bioactive glass-ceramic A-W". J Biomed Mater Res. (1990) 24(3): 331-343.

Koutsoukos et al., "Precipitation of calcium carbonate in aqueous solutions". J Chem Soc., Faraday Trans. 1, Physical Chemistry in Condensed Phases, (1984) 80(5): 1181-1192.

Lu et al., "Theoretical Analysis of Calcium Phosphate precipitation in simulated Body Fluid". Biomaterials (2005) 26(10): 1097-1108—Pre-Pub. Version by Hong Kong University of Science and Technology, Department of Mechanical Engineering, Kowloon; 34 pages.

Molvinger et al., "Porous chitosan-silica hybrid microspheres as a potential catalyst". Chem Mater. (2004) 16(17): 3367-3372.

Monmaturapoj et al., "Influence of preparation method on hydroxyapatite porous scaffolds". Bull Mater Sci. (2011) 34(7): 1733-1737.

Manoli et al., "Crystallization of calcite on chitin". J Cryst Growth, (1997) 182(1-2): 116-124.

Mushroom Source, "Aspen Wood Shavings for Mushroom Cultivation", Website (2015) in 2 pages.

National Institute of Health (NIH/NIBIB), "Tissue Engineering and Regenerative Medicine", Retrieved Sep. 24, 2018 from https://www.nibib.nih.gov/science-education/science-topics/tissue-engineering-and-regenerative-medicine in 13 pages.

Passauer U. et al., "Pilze in Höhlen" [Cave Mushrooms]. Denisia (2016) 37: 211-224.

Stewart B., "Concrete Fence Posts: Fact Sheet", Texas Agriculture Extension Service, Texas A & M University (1975) Article L-1368 in 4 pages.

Trinci et al., "II. Unrestricted Growth of Fungal Mycelia", The Mycota - Growth, Differenciation and Sexuality by Wessels et al. [Eds], Springer, Berlin, Heidelberg, (1994) Chapter II: 175-193.

Udawaitte et al., "Solidification of xonotlite fibers with chitosan by hydrothermal hot pressing". J Mater Sci. Lttrs. (2000) 45(6): 298-301.

University of Sydney, "Competition Between Fungi". Webpage, accessed 7/16/2014-http://bugs.bio.usyd.edu.au/learning/resources/Mycology/Ecology/competition.shtml in 3 pages.

Varma et al., "Porous calcium phosphate coating over phosphorylated chitosan film by a biomimetic method". Biomaterials (1999) 20(9): 879-884.

Wagner A. "Mycelium Biking—Eco-Design at its Best", Master's Thesis at Lulea University of Technology (2016) in 92 pages.

Wan-Mohtar et al., "The morphology of Ganoderma lucidum mycelium in a repeated-batch fermentation for exopolysaccharide production", Biotechnology Reports (2016) 11:2-11.

Weaver et al., "The stomatopod dactyl club: a formidable damage-tolerant biological hammer". Science (2012) 336(6086): 1275-1280.

Williams, J. "Growth Industry", Financial Times Jan. 12, 2019 (Mogu—Radical by Nature); download from URL <: https://mogu.bio/growth-industry-financial-times-uk-article/> in 1 page.

Woller R. "The Pearl Oyster Mushroom", University of Wisconsin Website (2011) in 2 pages.

Wösten et al., "Growing Fungi Structures in Space", ACT Research Category/Space Architecture; Noordwijk, The Netherlands (Oct. 15, 2018) in 17 pages.

Yamasaki et al., "A hydrothermal hot-pressing method: Apparatus and Application". J Mater Sci Lttrs. (1986) 5(3): 355-356.

(56) References Cited

OTHER PUBLICATIONS

Zivanovic et al., "Changes in Mushroom Texture and Cell Wall Composition Affected by Thermal Processing". J Food Service (2004) 69: 44-49.

Meyer et al., "Comparison of the Technical Performance of Leather, Artificial Leather, and Trendy Alternatives." Coatings (Feb. 2021) 11(2): 226; 14 pages.

Abbadi et al., "Immunocytochemical identification and localization of lipase in cells of the mycelium of Penicillium cyclopium variety", Applied Microbial Cell Physiology (1995) 42: 923-930.

Ando et al., "Cosmetic material for skin whitening - contains mushroom mycelium cultured matter and e.g. ginseng extract, chondroitin sodium sulphate and/or hyaluronic acid", WPI/THOMSON (1992-01-14), 1992(8): Accession #1992-062018; Abstract of JP4009316A; in 9 pages.

Attias et al., "Biofabrication of Nanocellulose-Mycelium Hybrid Materials", Adv Sustainable Syst. (2020) 5(2): 2000196 in 12 pages; Supporting Information in 7 pages.

Borräs et al., "Trametes versicolor pellets production: Low-cost medium and scale-up", Biochem Eng J. (2008) 42(1): 61-66.

Green et al., "Mechanical Properties of Wood", Forest Products Laboratory, 1999. in Wood Handbook—Wood as an engineering material. Gen Tech. Rep. FPL-GTR-113, Chapter 4 in 46 pages.

Holt et al. "Fungal mycelium and cotton plant materials in the manufacture of biodegradable molded packaging material: Evaluation study of select blends of cotton byproducts." J Biobased Mater Bioenergy (2012) 6(4): 431-439.

Jiang et al., "Manufacturing of Natural Composites with a Mycelium Binder and Vacuum-infused Vegetable Oil-based Resins", Poster dated May 2014; 1 page.

Jiang et al., "Vacuum Infusion of Mycelium-Bound Biocomposite Preforms with Natural Resins", CAMX ExpoConference Proceedings, Oct. 13-16, 2014, 13 pages.

Jones et al., "Mycelim Composites: A Review of Engineering Characteristics and Growth Kinetics", J Bionanoscience (2017) 11 (4): 241-257.

Jones et al., "Waste-derived Low-cost Mycelium Composite Construction Materials with Improved Fire Safety", FAM (Fire and Materials) (2018) 42(7): 816-825.

Kuhn et al., [Eds.] Cell Walls and Membranes in Fungi—An Introduction (Abstract) in Biochemistry of Cell Walls and Membranes in Fungi, Chapter 1, Springer Verlag Berlin/Heidelberg 1990, 2 pages.

Pathway-27, "Beta-glucan", Aug. 2012, retrieved from http://http://www.pathway27.eu/topstory/beta-glucan/ on Oct. 7, 2021 in 2 pages.

Vetchinkina et al., "Bioreduction of Gold (III) Ions from Hydrogen Tetrachloaurate. . . " Scientific Practical J Health Life Sciences No. 4, ISSN 22188-2268, (2013) pp. 51-56.

Wösten et al., "How a fungus escapes the water to grow into the air", Current Biology. (1999) 9(2): 85-88.

Zeng Z., "Cosmetic composition for cleaning skin, comprises glossy ganoderma spores and collagens, content of glossy ganoderma spores in composition and content of collagens in composition", WPI/Thomson (Feb. 5, 2006) 7: Accession #2007-057767; Abstract of CN1732887A; in 11 pages.

Ziegler et al., "Evaluation of Physico-mechanical Properties of Mycelium Reinforced Green Biocomposites Made from Cellulosic Fibers", Appl Engin Agricult. (2016) 32(6): 931-938.

\* cited by examiner

MYCOLOGICAL BIOPOLYMERS GROWN IN VOID SPACE TOOLING

This application claims the benefit of Provisional Patent Application No. 61/860,394 filed Jul. 31, 2013.

This invention relates to mycological biopolymers grown in void space tooling.

BACKGROUND OF THE INVENTION

As is known from U.S. Ser. No. 12/001,556, filed Dec. 12, 2007, a self-supporting composite material may be made of a substrate of discrete particles and a network of interconnected mycelia cells extending through and around the discrete particles and bonding the discrete particles together. In general, these composite materials may be classified as mycological biocomposites comprised of lignocellulosic waste materials, fungal cellular tissue, and potentially supplemental nutrients (minerals, vitamins, and the like).

As is also known from pending U.S. patent application Ser. No. 13/411,877, there is a potential to introduce variations in functionalization while maintaining continuous, porous, or structural hyphal morphology in the event that mycelial tissue is grown into a biocomposite, or combined with lignocellulosic waste and/or combinations of other additives.

It is an object of the invention to provide a mycological biopolymer material for use in making functional products.

It is another object of the invention to provide simple economical techniques for making mycological biopolymer products.

Briefly, the invention provides a material composed entirely of fungal mycelium, herein referred to as "mycological biopolymer." Mycological biopolymer has a wide range of material applications, based on the growth and processing of material, which include: structural composite cores, athletic workout mats, shoe soles, and the like.

Unlike mycological biocomposites which are comprised of lignocellulosic waste materials, fungal cellular tissue, and potentially supplemental nutrients (minerals, vitamins, and the like), the mycological biopolymer product consists entirely of fungal mycelium. This mycological biopolymer is home compostable and is a green alternative to products currently used in the industry, such as: ethylene vinyl acetate foams, polyvinyl chloride plastics, polyurethane foams, and the like. This technology may be used for applications currently employing non-renewable to slow-renewable substrates, which require high-energy inputs, multiple costly ingredients, and non-desirable chemical inputs.

The mycological biopolymer provides a low embodied energy, natural, and compostable alternative to conventional expanded foams. This bio-based industrial product is up-cycled from domestic agricultural lignocellulosic waste, sourced regionally (within 500 miles), and promotes the growth of the agriculture industry while reducing cumulative usage of fossil fuels. The biopolymer negates the need for conventional, energy-intensive, chemical extraction, refinement, and synthesis of expanded foams. The product of the invention literally grows itself, using little to no energy to produce the biopolymer apart from the energy used in sterilization, growth conditions, and drying.

The invention also provides a process for making the mycological biopolymer which uses a tooling paradigm that exploits the tendency of the fungus to grow toward a lower carbon dioxide content environment. The tools are designed to regulate the area in which the colonized material is in contact with regulated environmental conditions.

In one embodiment, the tooling includes tool to contain a nutritive substrate inoculated with the selected fungus and a lid on the tool to contain the nutritive substrate inoculated with the selected fungus in a sealed environment, except for a void space, which space is subsequently filled with a network of undifferentiated fungal mycelium in accordance with the invention.

The environmental conditions for producing the mycological biopolymer product, i.e. a high carbon dioxide ($CO_2$) content (from 5% to 7% by volume) and an elevated temperature (from 85° F. to 95° F.), prevent full differentiation of the fungus into a mushroom. There are no stipe, cap, or spores produced. The elevated temperature accelerates tissue production. The biopolymer product grows into the void space of the tool, filling the space with an undifferentiated mycelium chitin-polymer, which is subsequently extracted from the substrate and dried.

In one embodiment, in a first step, a tool is provided that defines a cavity and a lid is provided which seals at the edges of the tool and has an opening which creates a void space. For example, the tool is made of polycarbonate and is 21 inches by 13 inches by 2 inches with a completely open top. The lid is made of polyethylene plastic and seals along the top edge of the tool. The center of the lid has a 12 inch by 6 inch opening, which is surrounded by 1 inch high walls.

Next, the cavity of the tool is packed with nutritive substrate and spawn (i.e. a selected fungus) and the substrate is flattened across the top of the tool using a smoothing plate.

Thereafter, the lid is placed on the tool, sealing the top edges of the tool and providing an enclosed space containing the substrate and spawn as well as a void space within the lid. This combination of tool and lid provides only one outlet open to the controlled environmental conditions.

The fungus is then allowed to grow mycelium within the cavity and the mycelium respirates within the tool thereby producing carbon dioxide while colonizing the nutritive substrate.

During this time, the produced carbon dioxide is trapped in the tool and diffuses out of the outlet in the lid to create a gradient of carbon dioxide while the mycelia, searching for a more habitable environment, is allowed to grow along the gradient out of the cavity of the tool and to fill the void space within the lid without producing a stipe, cap or spore therein and to produce an entirely mycelium biopolymer.

The mycological biopolymer product can be used as a composite core to replace balsa, honeycomb, synthetic foams and aluminum. This technology offers several energy reducing benefits because the product grows itself in a matter of days. Additionally, the product can be grown through the reinforcement layer of traditional composites. This reinforcement layer can be composed of any material that mycelium can grow through (pore size larger than 1 microns). These layers can be suspended in the void space created by the tooling that is filled with biopolymer during incubation. These reinforcement layers are then incorporated into the biopolymer producing a pre-form of the composite core and reinforcement layers.

A laminate can be bound to the pre-form of composite core and reinforcement layers by extracting the pre-form from the substrate, and incubating the pre-form against the laminate material. This eliminates the need for the energy intensive process of setting and curing the layers of a traditional composite to adhere them, which typically involves autoclaving the materials. This also reduces the use of toxic adhesives, time, and labor needed to produce composites.

Finally, the biopolymer is compostable, so at the end of life, the core material can be degraded away from any synthetic reinforcement layer or laminates, and the synthetic reinforcement layer or laminates can be recycled.

These and other objects of the invention will become more apparent from the following description taken in conjunction with the drawings wherein.

Figure 7:
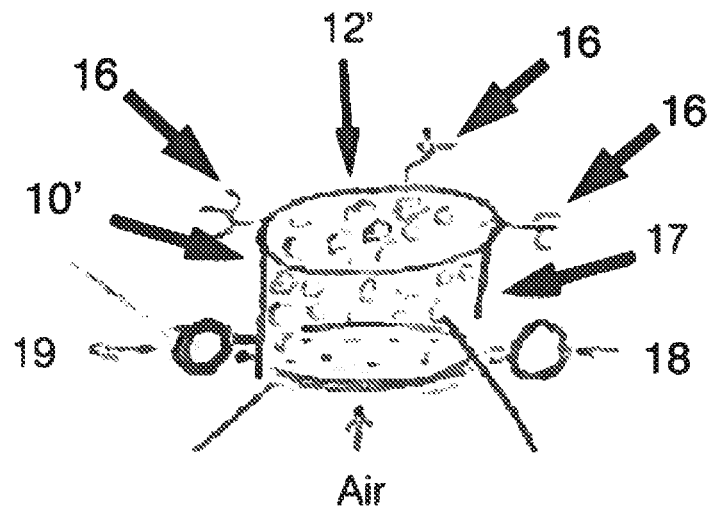
Figure 8:
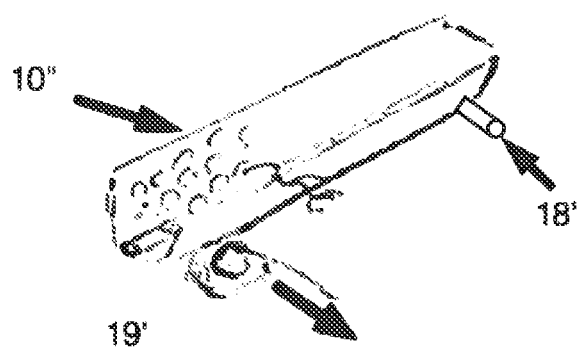
Figure 9:
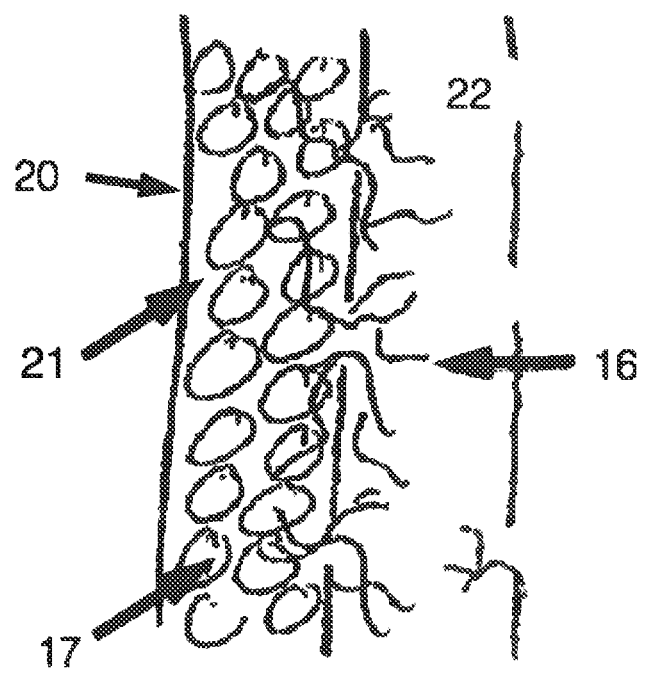

FIG. 7 schematically illustrates a hydroponic tool for growing biopolymer in accordance with the invention;

FIG. 8 illustrates a modified hydroponic tool for growing biopolymer in accordance with the invention; and FIG. 9 illustrates a further hydroponic tool for growing biopolymer in accordance with the invention.

Figure 1:
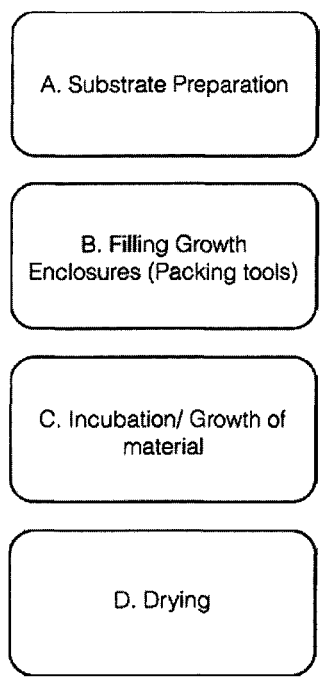
FIG. 1 illustrates a flow diagram of a general process for growing biopolymer in accordance with the invention.

Referring to FIG. 1, the process for making a mycological biopolymer product in accordance with the invention entails a first step A of substrate preparation which includes:
- A.1—mixing of nutrient components and water
- A.2—sterilization
- A.3—inoculation of substrate with mushroom tissue
- A.4—mixing of all components The next step B is to obtain a packing tool and includes:
- B.1—filling the tool with the prepared substrate
- B.2—leveling the surface of the substrate with a smoothing plate
- B.3—placing a lid on the tool and sealing the tool while forming a void space The next step C involves the incubation and growth of the mycelium and includes:
- C.1—precolonization for up to four days to allow mycelium to access nutrients prior to biopolymer growth
- C.2—incubation at high temperatures and carbon dioxide concentrations to induce biopolymer growth wherein the environmental temperature is from 85° F. to 95° F. and carbon dioxide constitutes from 3% to 7% of the environment within the void space.

The last step D involves drying of the produced biopolymer product, for example by:
- D.1—convection
- D.2—conduction
- D.3—microwave
- D.4—freeze drying FIG. 1 graphically illustrates the general process for growing biopolymer. All following flow charts are an expansion of this general process, and will begin at step B packing tools. Substrate preparation (step A) is the same for all following applications.

Figure 4:
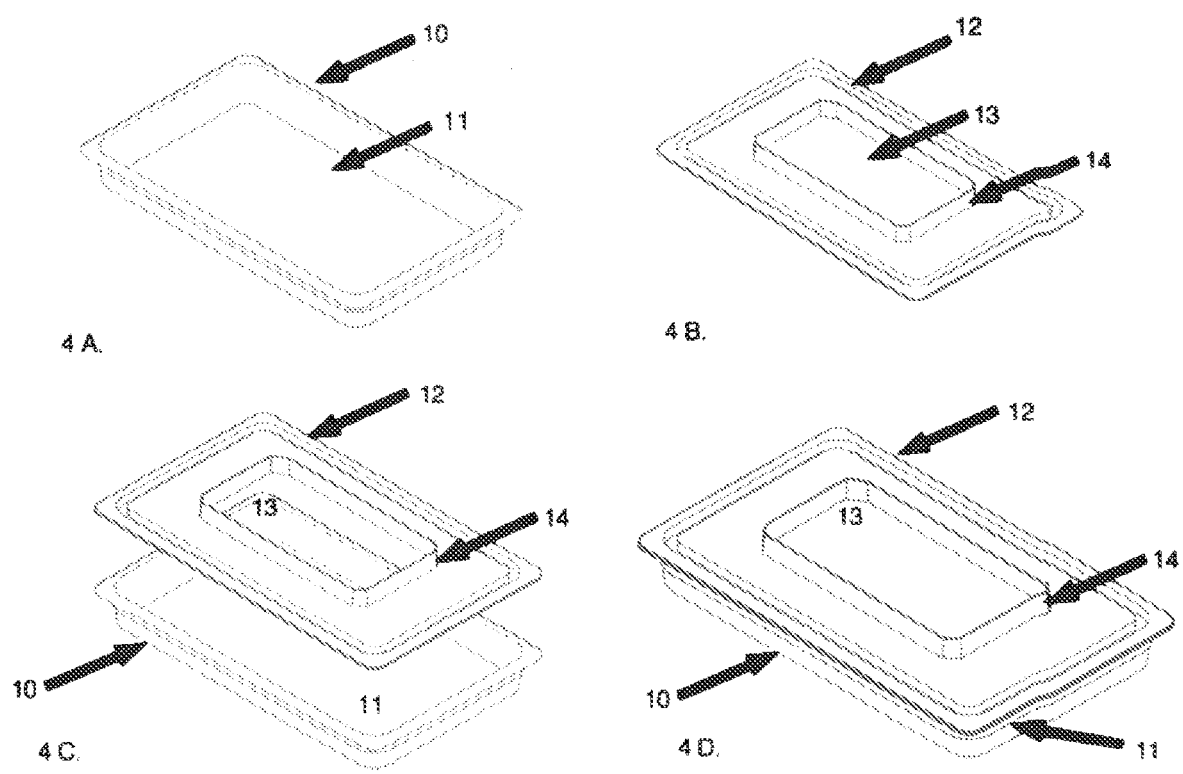
FIG. 4A illustrates a perspective view of a tool for growing biopolymer in accordance with the invention.
FIG. 4B illustrates a perspective view of a lid for placement on the tool of FIG. 4A.
FIG. 4C illustrates an exploded view of the tool and lid of FIGS. 4A and 4B when in place.
FIG. 4D illustrates a perspective view of the tool and lid of FIGS. 4A and 4B when in place.

Referring to FIG. 4A, by way of example, a tool 10 for growing biopolymer is of rectangular shape and defines a rectangular cavity 11 for receiving a substrate (not shown). The tool is made of polycarbonate and is 21 inches by 13 inches by 2 inches with a completely open top.

Referring to FIG. 4B, a lid 12 for sealing the tool 10 is also of rectangular shape to sit on the periphery of the tool in sealed relation (see FIGS. 4C and 4D) and has an opening 13 which creates a void space. For example, The lid 12 is made of polyethylene plastic and seals along the top edge of the tool 10. The center of the lid 12 has a 12 inch by 6 inch opening, which is surrounded by 1 inch high walls 14 to define the void space.

Figure 2:
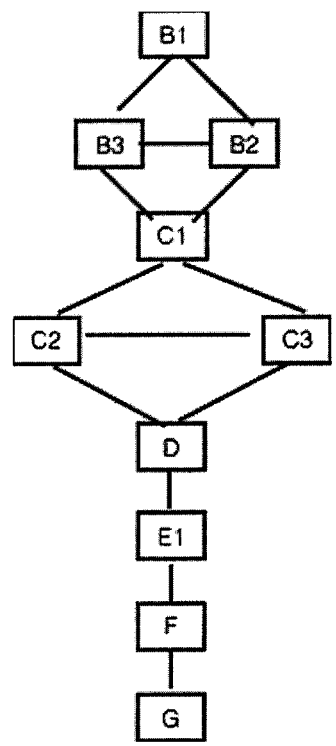
FIG. 2 illustrates a flow diagram of a process for producing biopolymer as a composite core replacement in accordance with the invention.

Referring to FIG. 2, the process for producing biopolymer as an expanded foam replacement includes a first step of substrate preparation, as above, followed by a step B of packing the substrate into a tool that includes:
- B.1—filling the tool with the prepared substrate, or
- B.2—suspending mats in the tool space to be filled with substrate in order to increase tensile strength in the finished product
- B.3—placing a lid on the tool and sealing the tool while forming a void space The next step C involves the incubation and growth of the mycelium and specifically includes:
- C.1—incubation at high temperatures and carbon dioxide concentrations For 5 to 14 days to induce biopolymer growth
- C.2—the environmental conditions may be altered after the material has reached a final volume in order to increase cross-linking and strength and/or
- C.3—various morphological modifiers may be sprayed onto the surface of the biopolymer or misted in the environment to alter the morphology of the mycelia, for example using hormones, forskolin, calcium, calcium blockers (cobalt chloride)

Figure 3:
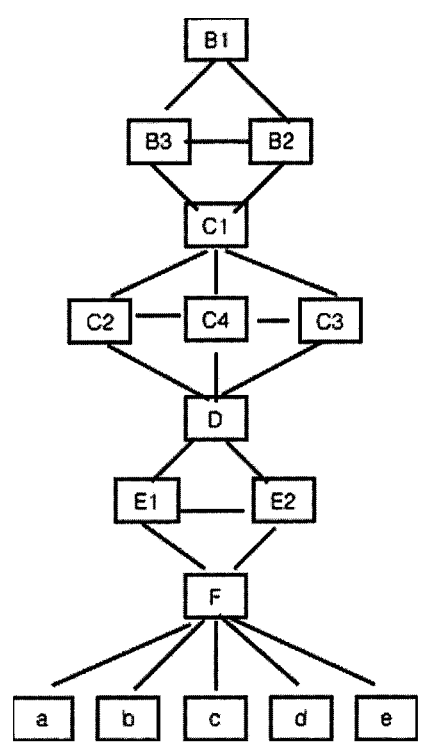
FIG. 3 illustrates a flow diagram of a process for the production of a composite core.
Figure 5:
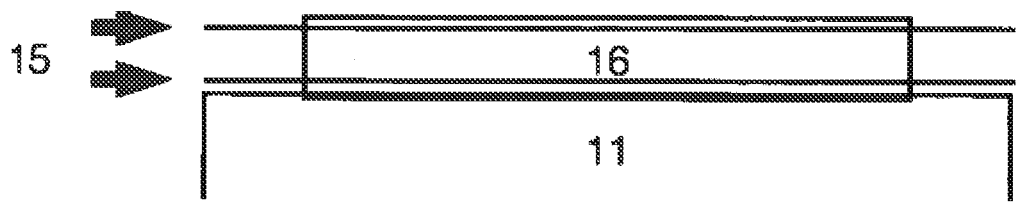
FIG. 5 illustrates the placement of reinforcement layers for incorporation into the final composite.

The next step D involves:
- D.1—extracting the biopolymer material from the space within the lid, for example, using a blade to separate the biopolymer material from the substrate These steps are followed by:
- E.1—compressing the biopolymer material to the desired dimensions and density or 3D shape and incubated for an additional 0 to 72 hours to increase strength and density
- F.1—material is freeze dried
- G.1—dried material is sanded, cut or milled to shape Referring to FIG. 3, the process for producing biopolymer as a composite core material includes a first step of substrate preparation, as above, followed by a step B of packing the substrate into a tool that includes:
- B.1—filling the tool with the prepared substrate, or
- B.2—suspending reinforcement layers of woven or non-woven mats in the tool space to be filled with substrate so that as the biopolymer grows within the tool space, the reinforcement layers will be incorporated into the core material being produced The next step C involves the incubation and growth of the mycelium and specifically includes:
- C.1—incubation at high temperatures and carbon dioxide concentrations for 5 to 14 days to induce biopolymer growth
- C.2—the environmental conditions may be altered after the material has reached a final volume in order to increase cross-linking and strength and/or
- C.3—various morphological modifiers may be sprayed onto the surface of the biopolymer or misted in the environment to alter the morphology of the mycelia, for example using hormones, forskolin, calcium, calcium blockers (cobalt chloride) and/or C.4—the biopolymer may be cut to shape and compressed vertically to increase strength and density The next step D involves:

D.1—extracting the biopolymer material from the nutritious substrate base in the tool, for example, using a blade These steps are followed by:

E.1—compressing the biopolymer material to the desired dimensions and density or 3D shape and incubated for an additional 12 to 72 hours to increase strength and density, and/or E.2—the biopolymer may be incubated while being sandwiched by a laminate material for an additional 0 to 72 hours with the growth allowing for adhesion to the laminate material F.1—the biopolymer material is then dried and/or compressed by any of the following methods or combinations thereof:
   a. conductively compressed
   b. conductive dried
   c. convective dried
   d. freeze dried
   e. microwave dried Referring to FIG. 5, the reinforcement mats 15 may be positioned horizontally, as viewed, to extend transversely across the biopolymer 16 and above the nutrient substrate 17 in order to be incorporated into the final composite.

Figure 6A:
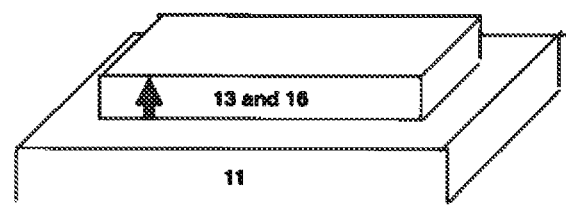
FIG. 6A illustrates a vertically disposed tool for growing biopolymer in accordance with the invention.
Figure 6B:
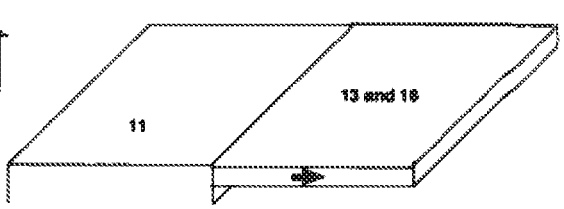
FIG. 6B illustrates a horizontally disposed tool for growing biopolymer in accordance with the invention.

Referring to FIGS. 6A and 6B, wherein like reference characters indicate like parts as above, the tooling for the growth of biopolymer 16 may be arranged for vertical growth or horizontal growth.

The orientation of growth, i.e. when the product is directed to grow either vertically (perpendicular from the substrate) or horizontally (laterally from the substrate) changes the morphology of the fungus and thus the mechanical characteristics of the product.

The tooling shown in FIGS. 6A and 6B are provided specifically to produce either vertical or horizontal mycelium by placing the void space (13—see FIG. 4D) to be filled with biopolymer on top of the substrate or to the side of the substrate. The tooling to produce vertical mycelium was provided with the shortest distance from the substrate surface, where carbon dioxide is produced, to the opening of the void space tool (not shown), allowing for fast diffusion, creating a homogenous environment (FIG. 6A). The horizontal tool has a much longer distance from the substrate surface to the opening, allowing for the production of a greater carbon dioxide gradient (FIG. 6B). Horizontal mycelium is produced when there is a differential in the atmosphere, causing the mycelium to grow along the plastic tooling towards an oxygen source.

These two types of biopolymer have two distinct morphologies; vertical mycelium growing upward from the surface of the substrate, and horizontal mycelium growing outwards along the plastic tooling away from the substrate.

Vertical mycelium (FIG. 6A) was shown to be composed of a highly integrated and un-oriented structure. While the structure making up the horizontal mycelium (FIG. 6B), is extremely aligned with a highly oriented network. These morphological differences have a great effect on the material properties of biopolymer produced. The horizontally grown biopolymer has greater tensile strength in the direction of growth, similar to the grain of balsa wood. The vertically grown biopolymer has the same strength characteristics in all directions, which is a benefit of this material because the material can be used in any orientation.

In order to increase the overall consistency of the material, the tools can be designed so that the open surface of substrate (exposed to the void space to be filled with biopolymer) has a more homogenous environment. The walls (14—see FIG. 4D) at the edge of the void space create a microenvironment that is different from that at the center of the void space. The environment regulates the fungal tissue physiology and morphology, affecting the final material characteristics. Reducing the wall height of the void space can increase the consistency of the environment, because the reduction in wall height minimizes the microenvironment effect of gasses settling within the walls of the void space. The wall height can be increased incrementally as the biopolymer fills the space to create larger materials. Additionally, a grid can be placed on the surface of the substrate, in the void space, in order create smaller pockets of microenvironments. This structure provides additional vertical surface area to promote consistent growth that is more evenly cross-linked. Prior to the completion of the growth the grid can be removed to permit the mycelium to conjoin with the adjacent tissues. Further, the grid can provide partitions that are designed to impart flexibility once the structure in removed and the mycological biopolymer is dried.

Nutrient and Water Addition

In order to scale this technology, it would be economical to develop a hydroponic system from which to grow biopolymer. This system would use an inorganic matrix that could be colonized by mycelium while it is fed by liquid nutrients, as shown in FIG. 7. This type of system would abolish the use of the organic substrate that is used for only one cycle of biopolymer growth, minimizing the waste that is generated. The system would allow for the use of waste liquid nutrients, such as spent brewers yeast. The use of liquid nutrients would increase efficiency of the system because the colonized inorganic matrix could be used for multiple cycles of biopolymer production, with nutrients continuously being pumped in while waste is pumped out.

Referring to FIG. 7, wherein like reference characters indicate like parts as above, use may be made of a hydroponic tool to produce the mycological biopolymer. As indicated, an inorganic matrix 17 is colonized with mycelium within a tool 10' of vertically disposed cylindrical shape with a lid 12', as above, and liquid nutrients are pumped through the matrix 17 via an inlet 18 and an outlet 19 continuously feeding the mycelium and removing waste. The relative humidity, temperature, carbon dioxide and oxygen levels are manipulated on the surface of the matrix 17 allowing for the production of the mycological biopolymer.

Referring to FIG. 8, wherein like reference characters indicate like parts as above, the tool 10" is disposed horizontally with an inlet 18' and outlet 19' for a flow through of liquid nutrients.

Referring to FIG. 9, wherein like reference characters indicate like parts as above, the tool 20 is vertically disposed with one chamber 21 to contain the inoculated substrate 17 and a second parallel chamber 22 to receive the mycological biopolymer 16. In the embodiment, the liquid nutrient may flow downwardly through the substrate 17 while the environmental air flows upwardly through the second chamber 22.

Regulating Morphology

As illustrated, the tool 20 has a vertically disposed wall separating the pair of vertically disposed chambers 21, 22 and having a plurality of openings communicating the chambers 21, 22 with each other.

In use, one chamber 21 is filled with a nutritive substrate and a fungus, i.e. an inoculated substrate 17 while the other chamber 22 is maintained with an environmental temperature in a range of from 85° F. to 95° F. with a carbon dioxide content of from 3% to 7%.

During incubation, at high temperatures and carbon dioxide biopolymer, growth is induced from the first chamber 21 through the openings in the wall into the other chamber 22 to produce a mycological biopolymer free of any stipe, cap or spores.

There are many ways to regulate the morphology and differentiation of the fungal tissue, and these techniques can be used to control the final material characteristics of the biopolymer material. Competitive species can be used to trigger differentiation and fruiting to enhance the efficiency of the material production system. Fungal hormones, such as 10-oxo-trans-8-decenoic acid (ODA), can be used in this way as well (PPA 61/951,056). Chemical supplements, such as forskolin, can also be added to the substrate, or misted onto the surface of growing biopolymer. Forskolin acts by activating that production of cAMP in the cell that triggers a signaling cascade, which increases the branching, or cross-linking, of the material. Finally, growing the material in an electric field will increase the alignment of hyphae, increasing the tensile strength in that direction. All of the techniques can be used to increase the consistency and efficiency of the material as well as the strength characteristics.

What is claimed is:

1. A process of growing a mycological biopolymer material, comprising the steps of
    providing a tool defining a cavity therein with an opening into said cavity;
    packing said cavity of the tool with nutritive substrate and a fungus;
    placing a lid on said tool to cover said cavity, said lid having only one outlet therein defining a void space open to fresh air;
    allowing said fungus to grow mycelium within said cavity and to allow the mycelium to respire within said cavity thereby producing carbon dioxide while colonizing the nutritive substrate;
    allowing the produced carbon dioxide to diffuse out of said outlet in said lid to create a gradient of carbon dioxide; and
    allowing the mycelium to grow along said gradient to fill said void space without producing a stipe, cap or spore therein and to produce a mycelium biopolymer in said void space.

2. The process of claim 1 wherein the carbon dioxide constitutes from 3% to 7% of the environment within said void space.

3. The process of claim 2 wherein the environmental temperature is from 85° F. to 95° F. within the void space.

4. The process of claim 1 wherein said void space is disposed vertically above said substrate.

5. The process of claim 1 wherein said void space is disposed horizontally beside said substrate.

6. The process of claim 1 further comprising the steps of:
    pumping a liquid nutrient through an inlet into said cavity for continuously feeding the mycelium; and
    removing waste from an outlet from said cavity.

7. A process of growing a mycological biopolymer comprising the steps of:
    filling a tool with a nutritive substrate and a fungus;
    placing a lid on the tool to cover the tool, said lid having only one outlet therein defining a void space open to fresh air,
    incubating the covered tool at high temperatures and carbon dioxide concentrations to induce mycological biopolymer growth into the void space without producing a stipe, cap or spore therein and wherein the environmental temperature is from 85° F. to 95° F. and carbon dioxide constitutes from 3% to 7% of the environment within the void space;
    removing the growth of mycological biopolymer from said void space; and
    thereafter drying the mycological biopolymer.

8. The process of claim 7 further comprising the steps of:
    suspending mats in the void space of the lid; and
    growing the mycological biopolymer about the mats to incorporate the mats in the mycological biopolymer to increase tensile strength in said mycological biopolymer.

9. The process of claim 7 wherein said step of incubating at high temperatures and carbon dioxide concentration occurs for 5 to 14 days.

10. The process of claim 7 further comprising the step of applying at least one morphological modifier onto a surface of the mycological biopolymer to alter the morphology of the mycelia.

11. The process of claim 10 wherein said morphological modifier is at least one of a hormone, forskolin, calcium, and a calcium blocker.

12. The process of claim 7 further comprising the step of compressing the mycological biopolymer to predetermined dimensions after said incubating step and thereafter incubating the compressed mycological biopolymer for up to 72 hours to increase strength and density prior to said step of drying.

13. The process of claim 12 further comprising the step of shaping the dried mycological biopolymer to a predetermined shape.

14. The process of claim 7 further comprising the step of sandwiching the mycological biopolymer between a pair of laminates after said incubating and thereafter incubating the mycological biopolymer for up to an additional 72 hours to adhere the mycological biopolymer between and to said pair of laminates prior to said step of drying.

15. A process of growing a mycological biopolymer comprising the steps of:
    providing a tool having a pair of vertically disposed chambers and a vertically disposed wall separating said chambers and having a plurality of openings communicating said chambers with each other;
    filling a first chamber of said vertically disposed chambers of the tool with a nutritive substrate and a fungus;
    passing a liquid nutrient through said substrate in said first chamber while passing environmental air through a second chamber of said vertically disposed chambers;
    maintaining the environmental temperature in the second chamber in a range of from 85° F. to 95° F. with a carbon dioxide content of from 3% to 7%; and
    incubating said substrate and fungus at high temperatures and carbon dioxide concentrations to induce biopolymer growth from said first chamber through said openings into said second chamber to produce a mycological biopolymer free of any stipe, cap or spores.

16. A process of growing a mycological biopolymer comprising the steps of:
placing an inoculated substrate containing a fungus for growing a mycological biopolymer in a chamber;
allowing said fungus to grow mycelium within said chamber and to allow the mycelium to respirate within said chamber thereby producing carbon dioxide;
allowing the produced carbon dioxide to diffuse out through a perforated barrier toward a lower content carbon dioxide environment to create a gradient of carbon dioxide; and
growing the mycological biopolymer from said substrate in said chamber through said barrier into said environment without producing a stipe, cap or spore.

17. The process of claim 16 wherein said environment has a carbon dioxide content of from 3% to 7% of said environment.

18. The process of claim 17 wherein said environment has a temperature of from 85° F. to 95° F.

19. The process of claim 16 wherein said environment is disposed vertically above said substrate.

20. The process of claim 16 wherein said environment is disposed horizontally of said substrate and said growing grows toward an oxygen source.

21. The process of claim 16 further comprising the step of flowing environmental air through said environment.

22. The process of claim 16, wherein the perforated barrier comprises a lid having only one outlet.

23. The process of claim 16, wherein the perforated barrier comprises a reinforcement layer.

24. The process of claim 23, wherein the reinforcement layer has a pore size greater than 1 micron.

25. The process of claim 23, wherein the reinforcement layer is a woven or non-woven mat.

26. The process of claim 15 further comprising the steps of:
removing the growth of mycological biopolymer from said second chamber; and
thereafter drying the mycological biopolymer.

27. The process of claim 15, wherein said step of incubating at high temperatures and carbon dioxide concentration occurs for 5 to 14 days.

28. The process of claim 15 further comprising the step of applying at least one morphological modifier onto a surface of the mycological biopolymer to alter the morphology of the mycelia.

29. The process of claim 28, wherein said morphological modifier is at least one of a hormone, forskolin, calcium, and a calcium blocker.

30. The process of claim 26 further comprising the step of compressing the mycological biopolymer to predetermined dimensions after said incubating step and thereafter incubating the compressed mycological biopolymer for up to 72 hours to increase strength and density prior to said step of drying.

31. The process of claim 30 further comprising the step of shaping the dried mycological biopolymer to a predetermined shape.

32. The process of claim 26 further comprising the step of sandwiching the mycological biopolymer between a pair of laminates after said incubating and thereafter incubating the mycological biopolymer for up to an additional 72 hours to adhere the mycological biopolymer between and to said pair of laminates prior to said step of drying.

* * * * *